United States Patent [19]

Lumma, Jr. et al.

[11] 4,091,101

[45] May 23, 1978

[54] 6-(1-PIPERAZINYL)QUINOXALINE

[75] Inventors: William C. Lumma, Jr., Pennsburg; Walfred S. Saari, Lansdale, both of Pa.

[73] Assignee: Merck & Co., Inc., Rahway, N.J.

[21] Appl. No.: 806,898

[22] Filed: Jun. 15, 1977

[51] Int. Cl.$^2$ .................. A61K 31/495; C07D 241/40
[52] U.S. Cl. ..................................... 424/250; 544/353; 544/395
[58] Field of Search ..................... 260/268 BC, 250 Q; 424/250

[56] References Cited

U.S. PATENT DOCUMENTS

| 3,538,097 | 11/1970 | Loewe et al. | 260/268 BC |
| 3,594,418 | 7/1971 | Gilbert | 260/250 Q |
| 3,919,223 | 11/1975 | Zmojdzin | 260/250 Q |

FOREIGN PATENT DOCUMENTS

| 1,440,722 | 6/1976 | United Kingdom | 260/268 BC |

*Primary Examiner*—Paul M. Coughlan, Jr.
*Attorney, Agent, or Firm*—Rudolph J. Anderson, Jr.; Mario A. Monaco; Martin L. Katz

[57] ABSTRACT

6-(1-Piperazinyl)quinoxaline and pharmaceutically acceptable salts thereof have serotoninmimetic activity. It is prepared by reducing the nitro group of 1-(3-amino-4-nitrophenyl)piperazine followed by treatment with glyoxal.

3 Claims, No Drawings

6-(1-PIPERAZINYL)QUINOXALINE

BACKGROUND OF THE INVENTION

This invention is concerned with 6-(1-piperazinyl)-quinoxaline and pharmaceutically acceptable salts thereof which demonstrate serotoninmimetic activity and hence are useful as anorectic, antidepressant, analgesic and hypnotic agents.

Several piperazinyl heterocycles are known in the art, for example, 2-(1-piperazinyl)quinoxalines (British Pat. No. 1,440,722); 4-(1-piperazinyl)quinazolines (U.S. Pat. No. 3,470,182); 2-(1-piperazinyl)quinolines (Rodriquez et al., European Journal of Pharmacology 24, 164-171 (1973); 4-(1-piperazinyl)cinnolines (U.S. Pat. Nos. 3,265,693 and 3,272,818); and 2-(1-piperazinyl)-pyrazines (Belgian Pat. No. 840,904). With this invention there is provided 6-(1-piperazinyl)quinoxaline with serotoninmimetic properties which exhibits anorectic antidepressant, analgesic and hypnotic activity. There is also provided a process for preparing the novel compound, pharmaceutical compositions comprising the novel compound, and a method of treatment comprising the administration of such compound and compositions.

DETAILED DESCRIPTION OF THE INVENTION

The novel compound of this invention has structural formula:

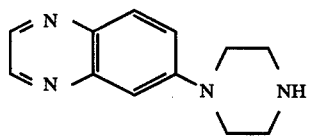

or a pharmaceutically acceptable salt thereof.

Also included within the scope of the present invention are non-toxic pharmaceutically acceptable salts. Such acid addition salts of the novel compound are formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, sulfuric acid, phosphoric acid, nitric acid, isethionic acid or the like.

The novel process of this invention comprises reducing the nitro group of 1-(3-amino-4-nitrophenyl) piperazine followed by condensation with glyoxal. The nitro group is readily reduced catalytically, prefereably with a palladium catalyst in a lower alkanol such as methanol or ethanol until three equivalents of hydrogen are absorbed. The temperature is not critical but the reduction is most conveniently run at ambient temperature (20°-25° C.). The alkanolic solution of the reduction product is then treated with approximately an equimolecular amount of glyoxal in aqueous solution. This reaction also proceeds rapidly at 20°-25° C.

A further embodiment of this invention is a method of producing an anorectic effect in patients in need of such treatment that comprises administering a therapeutically effective amount of the compound or compositions of the present invention. Typically the dosage level ranges from about 0.1 to about 500 mg./day, and preferably is from 0.1 to about 100 mg./day of the active principle of the present invention.

The compound of this invention also finds utility as an antidepressant, analgesic and hypnotic agent and for such purposes are administered as described above. Pharmaceutical compositions comprising the novel compound as active ingredient may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from about 0.1 to about 100 mg.

EXAMPLE 1

6-(1-Piperazinyl)quinoxaline acetate

Step A: Preparation of 1-(3-amino-4-nitrophenyl)piperazine hydrofluoride

A mixture of 31.8 g. (0.200 mol) of 2,4-difluoronitrobenzene, 13 g. of liquid ammonia and 100 ml. of dry ethanol is heated at 100° C. in a rocking bomb for 24 hours. The mixture is cooled, vented and diluted to 300 ml. with water and filtered to give 22.5 g. of 2-amino-4-fluoronitrobenzene, m.p. 91°-94° C.

The crude aminofluoronitrobenzene (15.9 g., 0.102 mol) is treated with 24 g. of piperazine in 80 ml. of acetonitrile for one hour at reflux. The mixture is cooled and filtered and the cake is dried to give 19 g. of 1-(3-amino-4-nitrophenyl)piperazine hydrofluoride, m.p. 228°-230° C. dec.

Step B: Preparation of 6-(1-Piperazinyl)quinoxaline acetate 1-(3-Amino-4-nitrophenyl)piperazine hydrofluoride (2.2 g., 0.0091 mol) is hydrogenated in 100 ml. of a 1:1 ethanol-water mixture in the presence of 1.1 g. of 10% Pd on carbon at an initial pressure of 35-40 psiq of hydrogen at ambient temperature. After three equivalents of hydrogen have been absorbed, the mixture is vented to nitrogen and filtered through diatomaceous earth into a flask containing 2 ml. of 40% (by weight) aqueous glyoxal. The total filtrate is concentrated under vacuum, the aqueous solution is basified with sodium hydroxide, and then extracted with chloroform. The chloroform extract is washed with water, dried over sodium sulfate and concentrated under vacuum to an oil which is treated with 50 ml. of ethanol and 2 ml. of 10N anhydrous ethanolic-hydrogen chloride. The precipitated hydrochloride is partitioned between aqueous sodium carbonate and methylenechloride and the methylene chloride extract is washed with water, dried over sodium sulfate and concentrated to an oil which is treated with 0.5 ml. of acetic acid in 40 ml. of isopropanol and 40 ml. of ether. The crystallized 6-(1-piperazinyl)quinoxaline acetate, m.p. 147°-148.5° C. is collected by filtration.

EXAMPLE 2

| Preparation of Capsule Formulation | |
|---|---|
| Ingredient | Milligrams per Tablet |
| 6-(1-piperazinyl)quinoxaline acetate | 6 |
| Starch | 87 |
| Magnesium stearate | 7 |

The active ingredient, starch and magnesium stearate are blended together. The mixture is used to fill hard shell capsules of a suitable size at a fill weight of 100 milligrams per capsule.

EXAMPLE 3

Preparation of Tablet Formulation

| Ingredient | Milligrams per Tablet |
| --- | --- |
| 6-(1-piperazinyl)quinoxaline acetate | 12 |
| Lactose | 200 |
| Corn Starch (for mix) | 50 |
| Corn Starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° C. The dry granules are passed through a No. 16 screen. The mixture is lubricated with magnesium stearate and compressed into tablets in a suitable tableting machine. Each tablet contains 12 milligrams of active ingredient.

What is claimed is:

1. The compound, 6-(1-piperazinyl)quinoxaline or a pharmaceutically acceptable salt thereof.

2. A method of producing an anorectic effect in a patient in need of such treatment comprising the administration of an effective amount of 6-(1-piperazinyl)quinoxaline or a pharmaceutically acceptable salt thereof.

3. A pharmaceutical anorectic composition comprising a pharmaceutical carrier and an effective amount of 6-(1-piperazinyl)quinoxaline or a pharmaceutically acceptable salt thereof.

* * * * *